(12) United States Patent
Sharma et al.

(10) Patent No.: US 10,024,787 B2
(45) Date of Patent: Jul. 17, 2018

(54) SYSTEM AND METHOD FOR MEASURING CONCENTRATION OF A TRACE GAS IN A GAS MIXTURE

(71) Applicant: General Electric Company, Schenectady, NY (US)

(72) Inventors: Rachit Sharma, Bangalore (IN); Chayan Mitra, Bangalore (IN); Sandip Maity, Bangalore (IN); Vinayak Tilak, Bangalore (IN); Xiaoyong Liu, Wellesley, MA (US); Anthony Kowal, Berlin, MA (US); Chong Tao, Billerica, MA (US)

(73) Assignee: General Electric Company, Schenectady, NY (US)

( * ) Notice: Subject to any disclaimer, the term of this patent is extended or adjusted under 35 U.S.C. 154(b) by 176 days.

(21) Appl. No.: 14/278,335

(22) Filed: May 15, 2014

(65) Prior Publication Data
US 2017/0003218 A1    Jan. 5, 2017

(51) Int. Cl.
*G01N 21/39*    (2006.01)
*G01N 21/03*    (2006.01)
(Continued)

(52) U.S. Cl.
CPC ........... *G01N 21/39* (2013.01); *G01N 21/274* (2013.01); *G01N 33/004* (2013.01); *G01N 2021/399* (2013.01); *G01N 2201/1218* (2013.01)

(58) Field of Classification Search
CPC ...... G01N 21/39; G01N 21/274; G01N 21/03; G01N 2201/12; G01N 2021/399; H01N 33/004
See application file for complete search history.

(56) References Cited

U.S. PATENT DOCUMENTS 3,979,589 A    9/1976    Sternberg et al.
4,589,971 A    5/1986    Mayeaux
(Continued)

FOREIGN PATENT DOCUMENTS

CN    1525157 A    9/2004
CN    1867820 A    11/2006
(Continued)

OTHER PUBLICATIONS

Owen, "Uses of Derivative Spectroscopy" Application Note, Agilent Technologies, 1995.*
(Continued)

*Primary Examiner* — Dominic J Bologna
(74) *Attorney, Agent, or Firm* — GE Global Patent Operation

(57) ABSTRACT

A method includes receiving a gas mixture at a first pressure including at least a primary gas and a secondary gas and changing a pressure of the received gas mixture from the first pressure to a second pressure. Further, the method includes determining a spectra of the gas mixture at the second pressure, wherein at least the first spectral line of the primary gas is spectrally distinguished from at least the second spectral line of the secondary gas, identifying a peak wavelength associated with the spectrally distinguished first spectral line of the primary gas based on at least two wavelengths of the secondary gas corresponding to at least two peak amplitudes in the spectra of the gas mixture, and determining a concentration of the primary gas based on the identified peak wavelength associated with the spectrally distinguished first spectral line of the primary gas.

17 Claims, 7 Drawing Sheets

(51) Int. Cl.
*G01N 21/27* (2006.01)
*G01N 33/00* (2006.01)

(56) References Cited

U.S. PATENT DOCUMENTS

| | | | |
|---|---|---|---|
| 5,317,156 | A | 5/1994 | Cooper et al. |
| 5,821,537 | A | 10/1998 | Ishihara et al. |
| 6,353,225 | B1 | 3/2002 | Strzoda et al. |
| 6,483,589 | B1 | 11/2002 | Suzuki et al. |
| 6,519,039 | B1 * | 2/2003 | Morishita ............ G01J 3/4338 356/437 |
| 6,552,792 | B1 | 4/2003 | Pilgrim et al. |
| 6,567,433 | B2 | 5/2003 | May |
| 6,611,341 | B2 | 8/2003 | May |
| 6,622,556 | B1 | 9/2003 | May |
| 6,633,593 | B2 | 10/2003 | Ksendzov et al. |
| 6,657,198 | B1 | 12/2003 | May |
| 6,671,296 | B2 | 12/2003 | May |
| 6,693,928 | B2 | 2/2004 | May |
| 6,775,001 | B2 | 8/2004 | Friberg et al. |
| 7,064,329 | B2 | 6/2006 | Webber |
| 7,075,653 | B1 | 7/2006 | Rutherford |
| 7,132,661 | B2 | 11/2006 | May |
| 7,166,843 | B2 | 1/2007 | May |
| 7,385,703 | B2 | 6/2008 | Berg |
| 7,502,115 | B2 | 3/2009 | Patel et al. |
| 7,508,521 | B2 | 3/2009 | Liu et al. |
| 7,511,802 | B2 | 3/2009 | Smith |
| 7,586,094 | B2 | 9/2009 | Liu et al. |
| 7,679,059 | B2 | 3/2010 | Zhou |
| 7,704,301 | B2 | 4/2010 | Zhou et al. |
| 7,728,978 | B2 | 6/2010 | Zhou et al. |
| 7,787,123 | B2 | 8/2010 | Howell |
| 7,829,046 | B2 | 11/2010 | Baum et al. |
| 8,064,052 | B2 | 11/2011 | Feitisch et al. |
| 8,121,798 | B2 | 2/2012 | Lippert et al. |
| 8,154,728 | B2 | 4/2012 | Hu et al. |
| 8,155,893 | B2 | 4/2012 | Cline et al. |
| 8,547,554 | B2 | 10/2013 | Liu et al. |
| 2003/0080295 | A1 | 5/2003 | Webber et al. |
| 2006/0263256 | A1 | 11/2006 | Koshel et al. |
| 2007/0081162 | A1 | 4/2007 | Roller et al. |
| 2008/0255769 | A1 | 10/2008 | Zhou et al. |
| 2010/0089117 | A1 | 4/2010 | Liu et al. |
| 2010/0091278 | A1 | 4/2010 | Liu et al. |
| 2010/0180667 | A1 | 7/2010 | Bender et al. |
| 2012/0176600 | A1 * | 7/2012 | Falk ................ G01N 21/65 356/51 |

FOREIGN PATENT DOCUMENTS

| | | |
|---|---|---|
| EP | 1860425 A1 | 11/2007 |
| JP | 6195229 A | 5/1986 |
| JP | 2000283915 A | 10/2000 |
| JP | 2000298095 A | 10/2000 |
| JP | 2001021493 A | 1/2001 |
| JP | 2002131228 A | 5/2002 |
| JP | 2007285823 A | 11/2007 |
| JP | 2011141155 A | 7/2011 |

OTHER PUBLICATIONS

Guo et al., "The Study Of The Concentration Of Carbon Monoxide Measured Based On 1.58um Tunable Semiconductor Laser", Optical Communications and Networks (ICOCN 2010), 9th International Conference , Issue Date : Oct. 24-27, 2010, pp. 81-86.

Xiaoyong Frank Liu et al., filed Aug. 17, 2011, U.S. Appl. No. 13/211,821.

Gengliang, "Method and Instrument for Determining Water Content/Water Dew-Point of Natural Gas", Petroleum Instruments, vol. No. 14, Issue No. 4, pp. 43-46, 2008.

Cormeir et al., "Application of Computation Fluid Dynamics for LNG Vapor Dispersion Modeling: Ḧ Study of Key Parameters", Prevention in the Process Industries, vol. No. 22, pp. 332-352, 2009.

US Non-Final Office Action issued in connection with related U.S. Appl. No. 13/211,821 dated Oct. 4, 2012.

Great Britain Search Report and Opinion issued in connection with related GB Application No. 1214393.9 dated Nov. 16, 2012.

US Final Office Action issued in connection with related U.S. Appl. No. 13/211,821 dated Mar. 15, 2013.

Great Britain Office Action and Opinion issued in connection with related GB Application No. 1214393.9 dated Aug. 19, 2015.

Unofficial English Translation of Chinese Office Action issued in connection with related CN Application No. 201210293411.5 dated Nov. 5, 2015.

Unofficial English Translation of Japanese Office Action issued in connection with related JP Application No. 2012-180000 dated Apr. 26, 2016.

Great Britain Office Action and Opinion issued in connection with related GB Application No. 1214393.9 dated Jun. 3, 2016.

Unofficial English Translation of Japanese Search Report issued in connection with related JP Application No. 2012-180000 dated Feb. 7, 2017.

* cited by examiner

SYSTEM AND METHOD FOR MEASURING CONCENTRATION OF A TRACE GAS IN A GAS MIXTURE

BACKGROUND

The disclosure relates generally to spectroscopy, and more specifically to systems and methods for measuring concentration of a trace gas in a gas mixture.

In a pipeline industry, an enormous amount of natural gas is transferred on a daily basis for applications such as power generation. This natural gas may include critical trace gas contaminants that may be hazardous in some circumstances. Also, these trace gas contaminants may cause damage to machinery, increase production costs, and/or degrade product quality and product value in industrial, chemical, medical, pharmacological, and energy applications. Thus, it is very important to detect and measure concentration of trace gas contaminants in the natural gas.

Typically, one or more trace gases in a gas stream may have interfering absorption from background gas, which in turn limits detection sensitivity or even may prevent detection of trace gas contaminants. In one of the conventional techniques, a differential spectroscopy may be employed to reduce spectral interference of one or more trace gases from the background gas. In the differential spectroscopy, a spectrum of the background gas is initially recorded. Further, this recorded spectrum of the background gas is subtracted from a spectrum of the natural gas to obtain a differential spectrum, which in turn is used to measure the concentration of a particular trace gas in the natural gas. However, this process requires a gas purifier and other requisite accessories to remove the trace gas from the natural gas to record the background spectrum, which may be costly. Additionally, this process requires a switch between the sample/natural gas to be analyzed and the reference/background gas, which may slow the system response time. Moreover, there is no guarantee that the spectral interference would be effectively removed because the spectra of the sample gas and the background gas are not recorded at the same time and may vary over time.

Accordingly, an approach that adequately addresses present issues regarding detecting trace gas and determining concentration of trace gas in natural gas is desirable.

BRIEF DESCRIPTION

In accordance with one embodiment described herein, a method is presented. The method includes receiving in a cell unit a gas mixture at a first pressure including at least a primary gas and a secondary gas, wherein at least a first spectral line of the primary gas interferes with at least a second spectral line of the secondary gas at the first pressure of the gas mixture. Further, the method includes changing a pressure of the received gas mixture in the cell unit from the first pressure to a second pressure. Also, the method includes using a sensor unit for determining a spectra of the gas mixture at the second pressure, wherein at least the first spectral line of the primary gas is spectrally distinguished from at least the second spectral line of the secondary gas, identifying a peak wavelength associated with the spectrally distinguished first spectral line of the primary gas based on at least two wavelengths of the secondary gas corresponding to at least two peak amplitudes in the spectra of the gas mixture, and determining a concentration of the primary gas based on the identified peak wavelength associated with the spectrally distinguished first spectral line of the primary gas.

In accordance with a further aspect of the present disclosure, a system is presented. The system includes a cell unit for receiving a gas mixture at a first pressure including at least a primary gas and a secondary gas, wherein at least a first spectral line of the primary gas interferes with at least a second spectral line of the secondary gas at the first pressure of the gas mixture. The system further includes a pumping unit coupled to the cell unit for changing a pressure of the received gas mixture from the first pressure to a second pressure. Also, the system includes a control unit for determining a derivative of a spectra of the gas mixture at the second pressure, wherein at least the first spectral line of the primary gas is spectrally distinguished from at least the second spectral line of the secondary gas, identifying a peak wavelength associated with the spectrally distinguished first spectral line of the primary gas based on at least two peak wavelengths of the secondary gas corresponding to at least two peak amplitudes in the derivative of the spectra, and determining a concentration of the primary gas based on the identified peak wavelength associated with the spectrally distinguished first spectral line of the primary gas.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

As will be described in detail hereinafter, various embodiments of an exemplary spectroscopy system for measuring concentration of a primary gas in a gas mixture and method for measuring concentration of the primary gas in the gas mixture are presented. By employing the methods and the various embodiments of the spectroscopy system described hereinafter, the concentration level of one or more gases in the gas mixture may be easily determined using a single light source and at a low cost. Also, the methods and the various embodiments of the spectroscopy system may include laser wavelength drift correction and sensor calibration, which in turn improves the accuracy in determining the concentration level of the one or more gases in the gas mixture.

Figure 1:
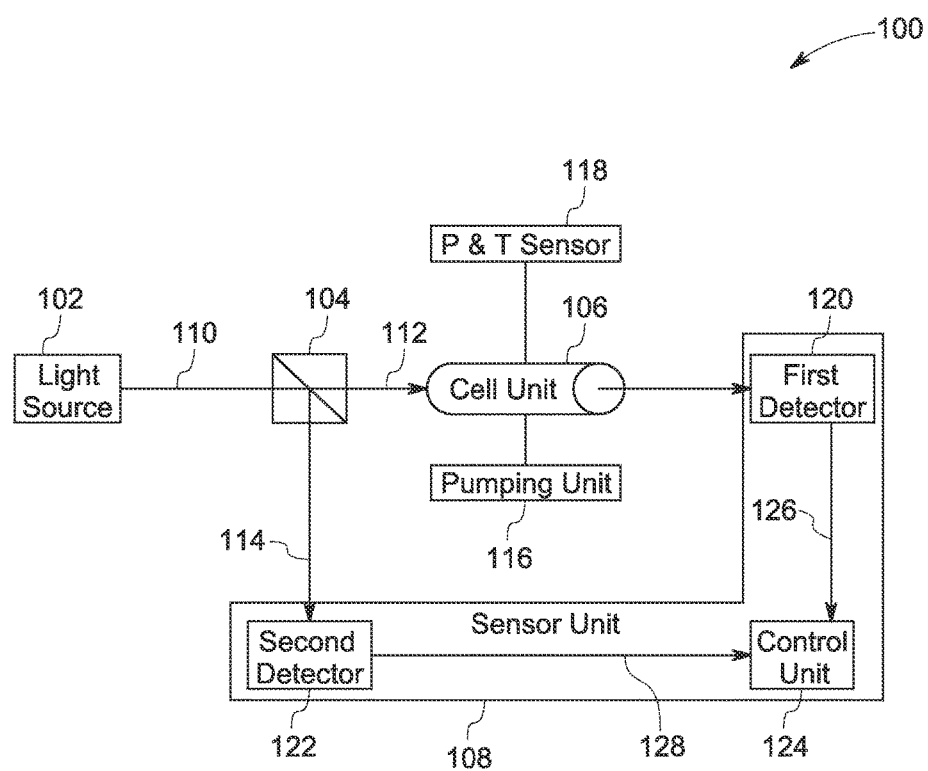
FIG. 1 is a diagrammatical representation of a spectroscopy system, in accordance with aspects of the present disclosure.

Turning now to the drawings, and referring to FIG. 1, a diagrammatical representation of a spectroscopy system 100, in accordance with aspects of the present disclosure, is depicted. The spectroscopy system 100 is configured to detect and measure concentration of a primary gas in a gas mixture. The primary gas may be referred to as a trace gas that is present in trace amounts in the gas mixture. One example of a primary gas is hydrogen sulfide ($H_2S$). In a more specific embodiment, the gas mixture may include a natural gas having one or more trace gases and background gases. The background gases may be referred to as gases that are relatively abundant in the gas mixture and are easier to detect and measure in the gas mixture than the primary or trace gases. One example of a background gas is carbon dioxide ($CO_2$). It may be noted that the background gas may also be referred to as a secondary gas in the present disclosure. Also, it may be noted that the concentration of one or more gases may be measured in terms of parts per million (PPM) in the gas mixture.

In the embodiment of FIG. 1, the spectroscopy system 100 includes a light source 102, a beam splitter 104, a cell unit 106, and a sensor unit 108. It may be noted that the spectroscopy system 100 may include other components and is not limited to the components shown in FIG. 1. The light source 102 is configured to emit a beam 110 towards the beam splitter 104. In the exemplary embodiment, a single light source, such as a modulated tunable diode laser, may be used for emitting the beam 110 having one or more spectra. In one example, the light source 102 may be a laser source and the beam 110 may be a laser beam. In this example, the light source 102 is selected or tuned to emit the beam 110 having a narrow spectral region that includes absorption bands of the primary gas and the secondary gas in the gas mixture and is selected to be narrower than a tuning range of the sensor unit 108.

Further, the emitted beam 110 is passed through the beam splitter 104 to split the beam 110 into a first beam 112 and a second beam 114. The second beam 114 may have a spectral region that is similar to a spectral region of the first beam 112. Also, in one example, the second beam 114 may be a duplicate of the first beam 112. Thereafter, the first beam 112 is passed through an absorbing media before reaching the sensor unit 108, while the second beam 114 may be passed directly to the sensor unit 108. Particularly, the first beam 112 is passed through the cell unit 106 that includes a sample of the gas mixture. The gas mixture may be a natural gas that includes one or more trace gases and one or more background gases. It may be noted that for ease of understanding, one of the trace gases, for example $H_2S$, is referred to as the primary gas and one of the background gases, for example $CO_2$, is referred to as the secondary gas, in the present disclosure.

Moreover, the cell unit 106 may include the gas mixture at a first pressure. For example, the first pressure may be about 760 torr. At this pressure, the absorption bands or spectrum of the primary gas and the secondary gas may interfere with each other. Such interferences cause independent detection of the primary gas to be a challenge. A pumping unit 116 such as, for example, a vacuum pump is coupled to the cell unit 106 to change the pressure of the gas mixture from the first pressure to a second pressure. In one example, the second pressure may be in a range from about 1 torr to about 300 torr. Particularly, the pumping unit 116 is used to reduce the pressure of the gas mixture to the second pressure to overcome the spectral interference of the primary gas and the secondary gas. In addition to the pumping unit 116, the cell unit may include a pressure and temperature (P&T) sensor 118 to sense the pressure and temperature of the gas mixture in real-time. The P&T sensor may comprise either an integrated sensor or separate pressure and temperature sensors. In one embodiment, the cell unit 106 may comprise a multi-pass cell structure that is filled with the gas mixture. Use of a multi-pass cell structure may aid in multiple reflections of the first beam 112 to achieve longer interaction lengths of about 100 meters, for example.

Furthermore, the first beam 112 that passes through the cell unit 106 provides spectra of the gas mixture for the original pressure condition and the modified pressure condition. When obtaining spectra, one or more gases in the gas mixture may absorb a portion of the first beam 112 while the first beam 112 is passing through the cell unit 106. This absorbed portion of the first beam 112 changes an intensity of the first beam 112 before the first beam 112 reaches the sensor unit 108. The changes in intensity of the first beam 112 as a function of wavelength is represented as the spectra of the gas mixture. Since the first beam 112 having the narrow spectral region is passed through the gas mixture, narrow spectra of the gas mixture is obtained at the sensor unit 108. The narrow spectra of the gas mixture may include the absorption bands or spectrum of the primary gas and the secondary gas. Particularly, the spectra of the gas mixture may include a summation of the spectrum of the primary gas and the spectrum of the secondary gas. It may be noted that the spectrum or absorption band of the primary gas is referred to as the first spectrum, while the spectrum or absorption band of the secondary gas is referred to as the second spectrum.

As will be appreciated, the first spectrum 204 (see FIG. 2) includes at least a first spectral line 212 that overlaps with a second spectral line 214 of the second spectrum 206 when the gas mixture is at the first pressure. Since these first and second spectral lines 212, 214 overlap with each other at the first pressure of the gas mixture, it will be very difficult for the sensor unit 108 to detect the first spectral line 212 of the primary gas and measure the concentration of the primary gas using the detected first spectral line 212.

In the exemplary embodiment, the pressure of the gas mixture is reduced from the first pressure to the second pressure to alter the spectra of the gas mixture so that the first spectral line of the primary gas may be spectrally distinguished from the second spectral line of the secondary gas. By lowering the pressure of the gas mixture, both narrow line-widths and line separation of the interfering spectral lines of the primary gas and the secondary gas can be achieved. In one embodiment, the first pressure of the gas mixture may not be reduced or changed if the first spectral line of the primary gas is already distinguished in the spectra of the gas mixture at the first pressure.

In one configuration, the sensor unit 108 includes a first detector 120, a second detector 122, and a control unit 124. The first detector 120 is positioned to receive the first beam 112 that is passed through the gas mixture. Also, the first detector 120 is configured to generate a first electrical signal 126 corresponding to the spectra of the gas mixture. In one example, the first detector 120 may comprise a photo detector. Similarly, the second detector 122 is positioned to receive the second beam 114 from the beam splitter 104. Further, the second detector 122 is configured to generate a second electrical signal 128 that is corresponding to spectra of the second beam 114. Since the second electrical signal 114 is directly received from the beam splitter 104, the second electrical signal 114 may be used to cancel out the effects of the inherent artifacts of the first beam 112. Thereafter, the generated first electrical signal 126 and the second electrical signal 128 are provided to the control unit 124 for determining the concentration of the primary gas in the gas mixture. Also, in one embodiment, the control unit 124 may be used to simultaneously determine the concentration of multiple gases in the gas mixture. For example, in FIG. 1, the control unit 124 may simultaneously determine the concentration of the primary gas and the secondary gas in the gas mixture.

Upon receiving the first electrical signal 126 and the second electrical signal 128, the control unit 124 may be configured to filter or remove noise in the first electrical signal 126 by using the second electrical signal 128. Further, the control unit 124 may process the first electrical signal to determine a derivative of the spectra of the gas mixture to spectrally distinguish the first spectral line of the primary gas from the second spectral line of the secondary gas. Particularly, in the derivative of the spectra of the gas mixture, the spectral lines may have narrower line-widths and sharper peak amplitudes. Thereafter, the control unit 124 may identify a peak wavelength associated with the spectrally distinguished first spectral line of the primary gas by using at least two peak wavelengths of the secondary gas corresponding to at least two peak amplitudes in the spectra of the gas mixture. Further, the control unit 124 may determine the concentration of the primary gas based on the identified peak wavelength associated with the spectrally distinguished first spectral line of the primary gas. The aspect of processing the first and second electrical signals 126, 128 and determining the concentration of the primary gas in the gas mixture will be explained in greater detail with reference to FIG. 4.

Figure 2:
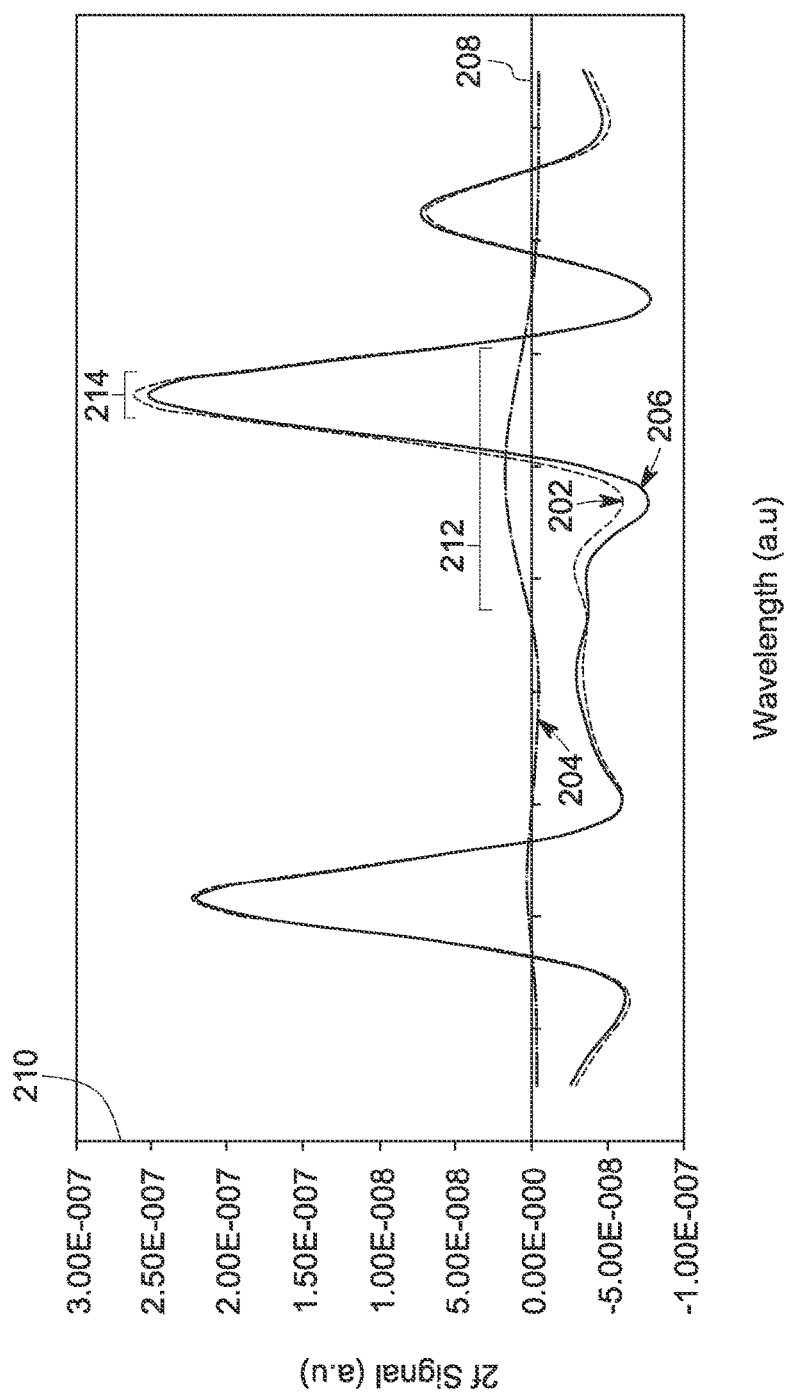
FIG. 2 is a graphical representation of a gas mixture at a first pressure, in accordance with aspects of the present disclosure.

Referring to FIG. 2, a graphical representation of a gas mixture at a first pressure, in accordance with aspects of the present disclosure, is depicted. Reference numeral 202 is representative of a derivative of the spectra of the gas mixture at the first pressure. Reference numeral 204 is representative of a derivative of a first spectrum of a primary gas, and reference numeral 206 is representative of a derivative of a second spectrum of a secondary gas. Also, reference numeral 208 represents an X-axis or wavelengths axis, while reference numeral 210 represents a Y-axis or absorption intensity axis. It may be noted that the spectra of the gas mixture includes a summation of the first spectrum and the second spectrum.

Particularly, in FIG. 2, a second derivative of the spectra of the gas mixture at the first pressure, for example 760 torr, is depicted. Since the secondary gas is relatively abundant in the gas mixture, the secondary gas may dominate the primary gas in the gas mixture. In FIG. 2, this is depicted by the derivative of the second spectrum or curve 206 that almost follows or overlaps on the derivative of the spectra or curve 202 of the gas mixture. On the other hand, the primary gas, which is a trace gas in the gas mixture, is present in trace amounts in the gas mixture. Thus, the derivative of the first spectrum 202 of the primary gas has low amplitude intensity, as depicted in FIG. 2. In addition, FIG. 2 depicts that when the gas mixture is at the first pressure, a first spectral line 212 of the derivative of the first spectrum 204 or the primary gas may spectrally interfere with a second spectral line 214 of the derivative of the second spectrum 206 or the secondary gas.

Figure 3:
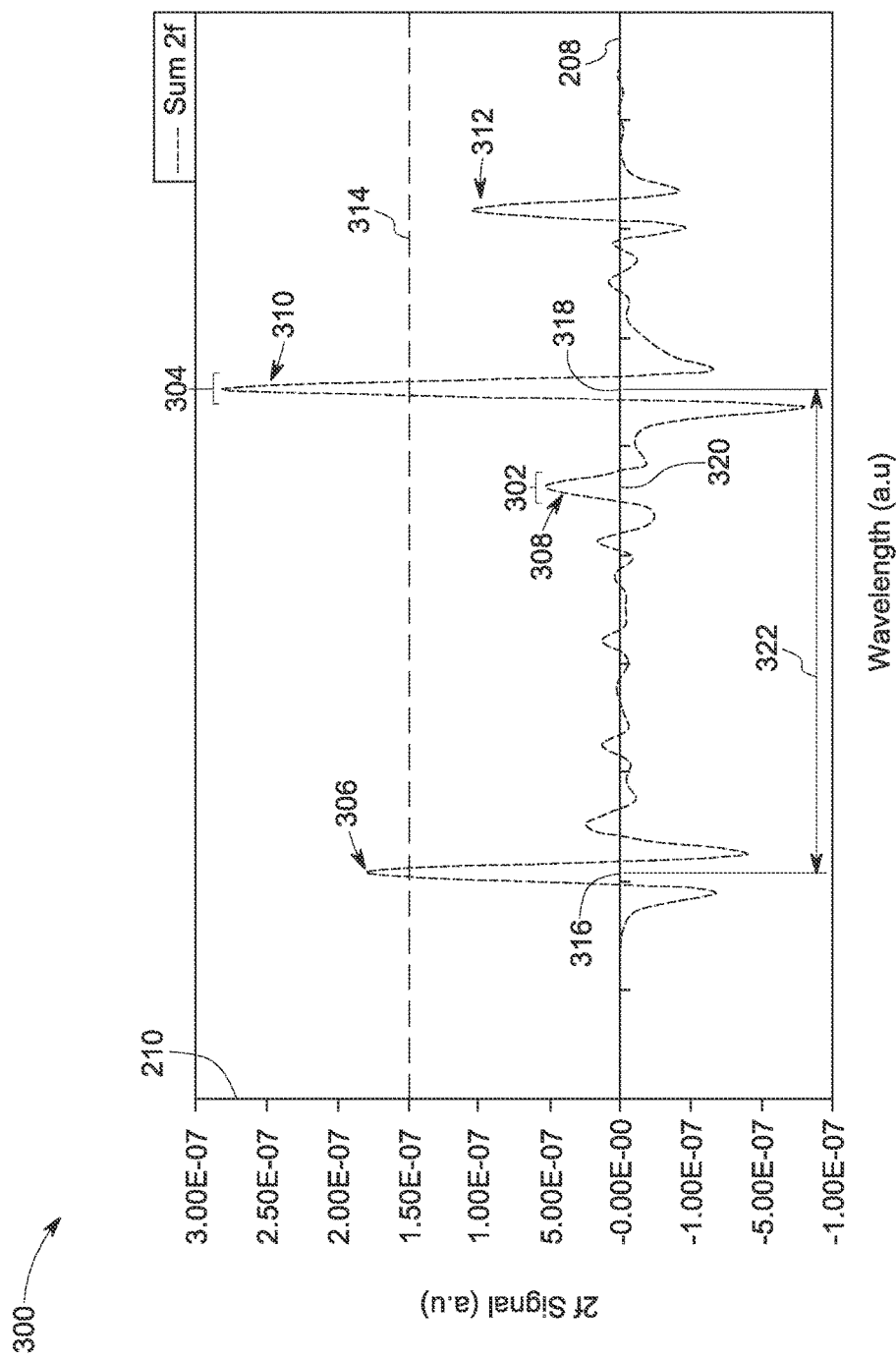
FIG. 3 is a graphical representation of the gas mixture at a second pressure, in accordance with aspects of the present disclosure.

To address the shortcomings associated with the spectra shown in FIG. 2, in the exemplary embodiment, the pressure of the gas mixture is reduced from the first pressure to a second pressure. In FIG. 3, a graphical representation of a derivative of the spectra 300 of the gas mixture at the second pressure is depicted. It may be noted that the terms "derivative of the spectra" and "derivative spectra" may be used interchangeably. In one example, the second pressure of the gas mixture is about 50 torr. By reducing the pressure of the gas mixture, the spectra of the gas mixture is altered to separate or enable the separation of at least one spectral line 302 of the primary gas from a second spectral line 304 of the secondary gas. The spectral line may be referred to as the portion of the spectra that indicates absorption intensity of a particular gas in the gas mixture. Further, by computing a second derivative of the spectra, narrow line widths and sharp peak amplitudes 306, 308, 310, 312 are achieved, as depicted in FIG. 3. Since the spectral lines 302, 304 are separated from each other and have sharp peak amplitudes 308, 310, the control unit 124 may easily detect a spectral line 302 corresponding to the primary gas and may use the detected spectral line 302 to determine the concentration of the primary gas.

Figure 4:
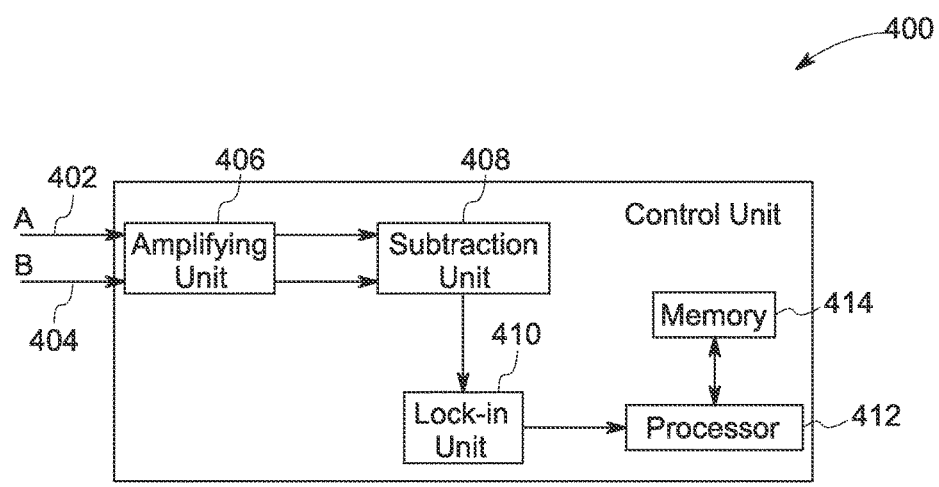
FIG. 4 is a diagrammatical representation of a control unit, in accordance with aspects of the present disclosure.

Referring to FIG. 4, a diagrammatical representation of a control unit 400, in accordance with aspects of the present disclosure, is depicted. For ease of understanding of the present disclosure, the control unit 400 is described with reference to the components and features of FIGS. 1-3. Reference numeral 400 is representative of a control unit 124, reference numeral 402 is representative of a first electrical signal 126, and reference numeral 404 is representative of a second electrical signal 128 in FIG. 1. As previously noted with reference to FIG. 1, the control unit 400 is configured to process the first electrical signal 402 and the second electrical signal 404 to detect a first spectral line 308 of the primary gas. Further, the control unit 400 is configured to determine a concentration of a primary gas 204 using the detected first spectral line 308 of the primary gas.

In a presently contemplated configuration, the control unit 400 includes an amplifying unit 406, a subtraction unit 408, a lock-in unit 410, a processor 412, and a memory 414. The amplifying unit 406 is configured to receive the first electrical signal 402 from the first detector 120 and the second electrical signal 404 from the second detector 122. Further, the amplifying unit 406 amplifies the received first and second electrical signals 402, 404 to increase the power of the signals 402, 404. In one example, the amplifying unit 406 may comprise a differential amplifier.

Thereafter, the subtraction unit 408, which may also be a signal processor, is coupled to the amplifying unit for reducing noise in the amplified electrical signal, filters noise in the amplified first electrical signal 402 by subtracting the amplified first electrical signal 402 with the amplified second electrical signal 404. Particularly, the subtraction unit 408 is used to cancel out the effects of the inherent artifacts of the first electrical signal 402. Furthermore, the lock-in unit 410, coupled to the subtraction unit, receives the filtered first electrical signal from the subtraction unit 408 and determines a derivative of the spectra 300 of the gas mixture from the filtered first electrical signal. In one specific embodiment, the lock-in unit 410 is used to determine a second derivative of the spectra of the gas mixture. In one example, the lock-in unit 410 may comprise a hardware or software lock-in amplifier.

Upon determining the derivative spectra 300 of the gas mixture, the processor 412 may detect the first spectral line 302 of the primary gas for determining the concentration of the primary gas. Particularly, the processor 412 may detect at least two wavelengths 316, 318 of the secondary gas using the peak amplitudes 306, 310 in the derivative spectra 300. In the exemplary embodiment, the processor 412 may first search for the peak amplitudes 306, 310 in one or more wavelength ranges including expected or pre-stored wavelengths. Further, the processor 412 may verify whether each of the peak amplitudes 306, 310 is above a threshold intensity range 314. Thereafter, the processor 412 may determine the wavelengths 316, 318 that are corresponding to the selected peak amplitudes 306, 310.

Furthermore, the processor 412 may identify a peak wavelength 320 associated with the spectrally distinguished first spectral line of the primary gas based on the determine wavelengths 316, 318 of the secondary gas. In one specific embodiment, the processor may calibrate the wavelength axis 208 prior to detecting the wavelength 320 of the primary gas. Calibration of the wavelength axis 208 is useful in a spectroscopy system to minimize error due to wavelength drift of the spectra of the gas mixture. In one example, the wavelength drift of the spectra of the gas mixture is mainly due to tuning properties of diode lasers, where the wavelength versus current relationship is prone to drift due to fluctuations of the thermoelectric cooler, the current source, or other operational/environmental parameters. Thus, for more reliable sensor performance, it is useful to periodically calibrate the tuning properties of the beam to avoid erroneous measurements.

To calibrate the wavelength axis 208, the processor may first compare the wavelengths 316, 318 of the secondary gas with expected or pre-stored wavelengths of the secondary gas. If the wavelengths 316, 318 are not same as the expected or pre-stored wavelengths, the processor 412 may adjust the derivative spectra 300 so that the wavelengths 316, 318 match the expected or pre-stored wavelengths. In one embodiment, the processor may assign new wavelength values across the wavelength axis 208 so that the values of the wavelengths 316, 318 match with the values of the expected or pre-stored wavelengths.

In this calibration-based embodiment, the processor 412 may then detect the peak wavelength 320 associated with the spectrally distinguished first spectral line 302 of the primary gas based on the two peak wavelengths 316, 318 of the secondary gas in the adjusted derivative spectra 300. The processor 412 may search for a peak wavelength in the adjusted derivative spectra 300. In one embodiment, the searching is around a wavelength that matches an expected or pre-stored peak wavelength of the primary gas. In one embodiment, the processor may search within a range including the two peak wavelengths 316, 318. Further, the processor 412 may represent the searched peak wavelength as the peak wavelength 320 associated with the spectrally distinguished first spectral line 302 of the primary gas.

In another specific embodiment, the processor 412 may determine the peak wavelength 320 associated with the spectrally distinguished first spectral line 302 of the primary gas without adjusting the derivative spectra 300 of the gas mixture or recalibrating the wavelength axis 208. In this embodiment, the processor may determine spectral separation 322 between the two identified peak wavelengths 316, 318 of the secondary gas. Thereafter, the processor 412 may detect the peak wavelength 320 of the primary gas within the determined spectral separation 322 at a location that is corresponding to a predefined function of the determined spectral separation 322. In one example, the processor 412 may detect a location on the wavelength axis 208 that is 60% of the spectral separation 322 from the peak wavelength 316 of the secondary gas. This 60% of the spectral separation 322 may be a predefined percentage of the spectral separation 322. It may be noted that the processor 412 may employ any ratio or function of the determined spectral separation 322 to detect the peak wavelength 320 of the primary gas.

Once the peak wavelength 320 is identified in the derivative spectra 300, the processor 412 may determine the concentration of the primary gas by using the first spectral line 302 that is distinguished from the second spectral line 310. In one example, the concentration of the primary gas is measured in terms of PPM level in the gas mixture by using the first spectral line 308. For example, the processor 412 may determine the concentration of the primary gas by computing peak amplitude 308 corresponding to the identified peak wavelength 320 of the primary gas. In one embodiment, a look-up table is used to determine the concentration of the primary gas that is corresponding to the absorption intensity or peak amplitude 308 of the first spectral line 302 of the primary gas. Further, in another embodiment, the processor 412 may simultaneously measure the concentration of the primary gas and the secondary gas using the spectrally distinguished first and second spectral lines 302, 304. Also, in addition to correcting the wavelength drift of the spectra, the processor may also re-calibrate the sensor unit 108 that is used for measuring the concentration of the primary gas. The aspect of re-calibrating the sensor unit 108 will be explained in greater detail with reference to FIG. 6. Thus, by employing the exemplary spectroscopy system, the concentration level of the primary gas in the gas mixture is accurately measured.

Figure 5:
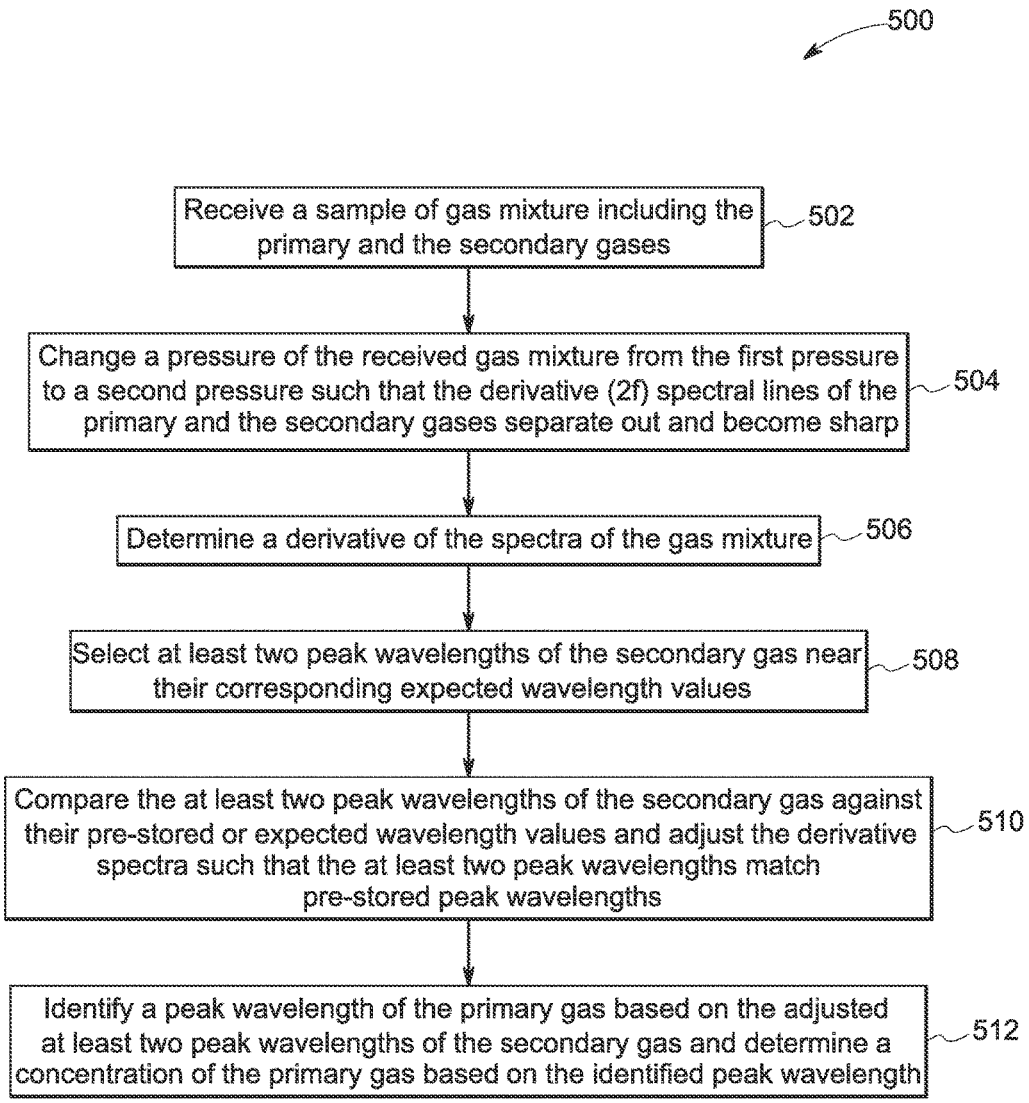
FIG. 5 is a flow chart illustrating a method for measuring concentration of a primary gas in the gas mixture, in accordance with aspects of the present disclosure.

Referring to FIG. 5, a flow chart illustrating a method for measuring concentration of a primary gas in a gas mixture, in accordance with aspects of the present disclosure, is depicted. For ease of understanding of the present disclosure, the method 500 is described with reference to the components and features of FIGS. 1-4. The method begins at step 502, where a sample of the gas mixture is received by a cell unit 106. The gas mixture may include at least a primary gas and a secondary gas. Also, the gas mixture is at a first pressure, for example 760 torr, in the cell unit 106, where a first spectral line of the primary gas interferes with at least a second spectral line of the secondary gas. Since the spectral lines of the primary and secondary gases are overlapping or interfering with each other at the first pressure, it will be very difficult for a spectroscopy system 100 to identify at least one spectral line of the primary gas and to measure the concentration of the primary gas using the identified spectral line.

At step 504, the pressure of the gas mixture in the cell unit 106 is changed from the first pressure to a second pressure. To that end, a pumping unit 116 that is coupled to the cell unit 106 is configured to change the pressure of the gas mixture from the first pressure to the second pressure. Particularly, the pressure of the gas mixture may be reduced to the second pressure to alter the spectra and to distinguish at least a first spectral line of the primary gas from a second spectral line of the secondary gas. In one embodiment, the pressure of the gas mixture may not be changed from the first pressure to the second pressure if the first spectral line of the primary gas is already distinguished in the spectra of the gas mixture at the first pressure.

Subsequently, at step 506, a derivative of the spectra of the gas mixture is determined to effectively distinguish the first spectral line of the primary gas from the second spectral line of the secondary gas. To that end, a control unit 124 is used to determine the derivative of the spectra of the gas mixture. Particularly, the control unit 124 may determine a second derivative of the spectra so that the spectral lines 302, 304 are separated and sharpened, as depicted in FIG. 3. Particularly, by taking the second derivative of the spectra, the widths of the peak amplitudes 306, 308, 310, 312 in the spectra are narrowed down and the amplitude intensity is increased (see FIG. 3). This in turn helps to identify the wavelengths 316, 318 of the secondary gas.

Additionally, at step 508, the two peak amplitudes 306, 310 of the secondary gas are identified. To that end, a processor 412 in the control unit 400 is used for searching the two peak amplitudes 306, 310 that are above threshold intensity 314. Particularly, the processor 412 may search in one or more ranges including expected or pre-stored wavelengths. The relative abundance of the secondary gas in the gas mixture may make the peak amplitudes 306, 310 corresponding to the secondary gas easier to detect. Thereafter, the processor 412 selects two peak wavelengths 316, 318 that are associated with the corresponding peak amplitudes 306, 310 in the secondary gas.

Furthermore, at step 510, the selected two peak wavelengths 316, 318 in the secondary gas are compared with their expected or pre-stored wavelength values to determine any wavelength drift in the derivative spectra 300 of the gas mixtures. To that end, the processor 412 in the control unit 400 compares at least two peak wavelengths 316, 318 of the secondary gas with the corresponding pre-stored or expected wavelength values to detect the drift in the wavelength of the derivative spectra. Further, upon determining the wavelength drift, the processor 412 may adjust the derivative spectra 300 such that the two peak wavelengths 316, 318 of the secondary gas match with the pre-stored or expected wavelengths. Thus, the secondary gas may be used as a reference gas or background gas to correct the wavelength drift in the spectra 202 of the gas mixture. Also, the processor 412 may use one of the peak amplitudes 310 corresponding to the adjusted peak wavelength 318 in the derivative spectra 300 to calculate the concentration of the secondary gas.

Further at step 512, the recalibrated wavelength axis 208 may be used to identify a peak wavelength 320 of the primary gas. In one embodiment of step 512, the processor 412 may identify a peak wavelength that is at or near an expected or pre-stored wavelength of the primary gas. The selected peak wavelength is represented as the peak wavelength 320 of the primary gas. In another embodiment, the processor may determine a spectral separation 322 between the two identified peak wavelengths 316, 318. In another embodiment of step 512, a function of the determined spectral separation 322 may be used by the processor 412 to detect the peak wavelength 320 of the primary gas. Thus, the peak wavelengths 316, 318 of the secondary gas may be used as reference wavelengths to help more efficiently identify the peak wavelength 320 of the primary gas In addition, the processor 412 may determine the concentration by computing peak amplitude 308 at the detected peak wavelength 320 of the primary gas. In one embodiment, the processor 412 may also recalibrate the sensor unit 106 or Y-axis 210 prior to measuring the concentration of the primary gas. This aspect of re-calibrating the sensor unit 108 will be explained with reference to FIG. 6. Additionally, the processor 412 may repeat the steps 502-512 for gas mixtures that are provided at subsequent points in time.

Figure 6:
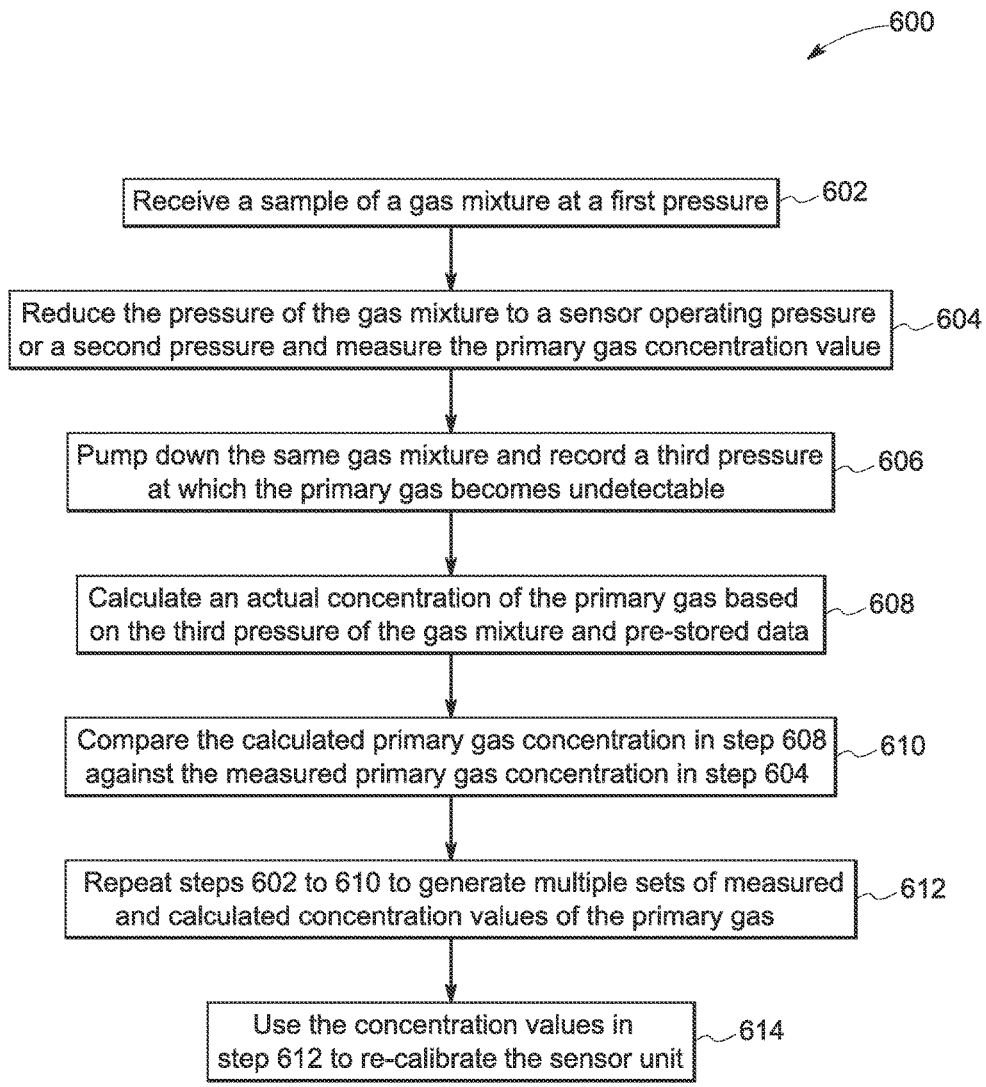
FIG. 6 is a flow chart illustrating a method for calibrating a sensor unit, in accordance with aspects of the present disclosure.

Referring to FIG. 6, a flow chart illustrating a method for calibrating a sensor unit, in accordance with aspects of the present disclosure, is depicted. If a sensor unit 108 operates continuously in a field, periodic calibration is useful to ensure that the sensor unit performance is not degraded over time. In most sensor units, the calibration may be performed offline using calibration gases. For ease of understanding of the present disclosure, the method 600 is described with reference to the components and features of FIGS. 1-4. The method begins at step 602, where a sample of a gas mixture is received by a cell unit 106 at a first pressure. The gas mixture may include at least a primary gas and a secondary gas.

Further, at step 604, the pressure of the gas mixture may be reduced or pumped from a first pressure to a second pressure. It may be noted that the terms "sensor operating pressure" and "second pressure" may be used interchangeably. Thereafter, sensor unit 108 is used to measure the concentration of the primary gas. Particularly, the control unit 124 may send a control signal to the pumping unit 116 to change the pressure of the gas mixture to the sensor operating pressure. Further, the control unit 124 may measure the concentration of the primary gas using the method 500 of FIG. 5.

Figure 7:
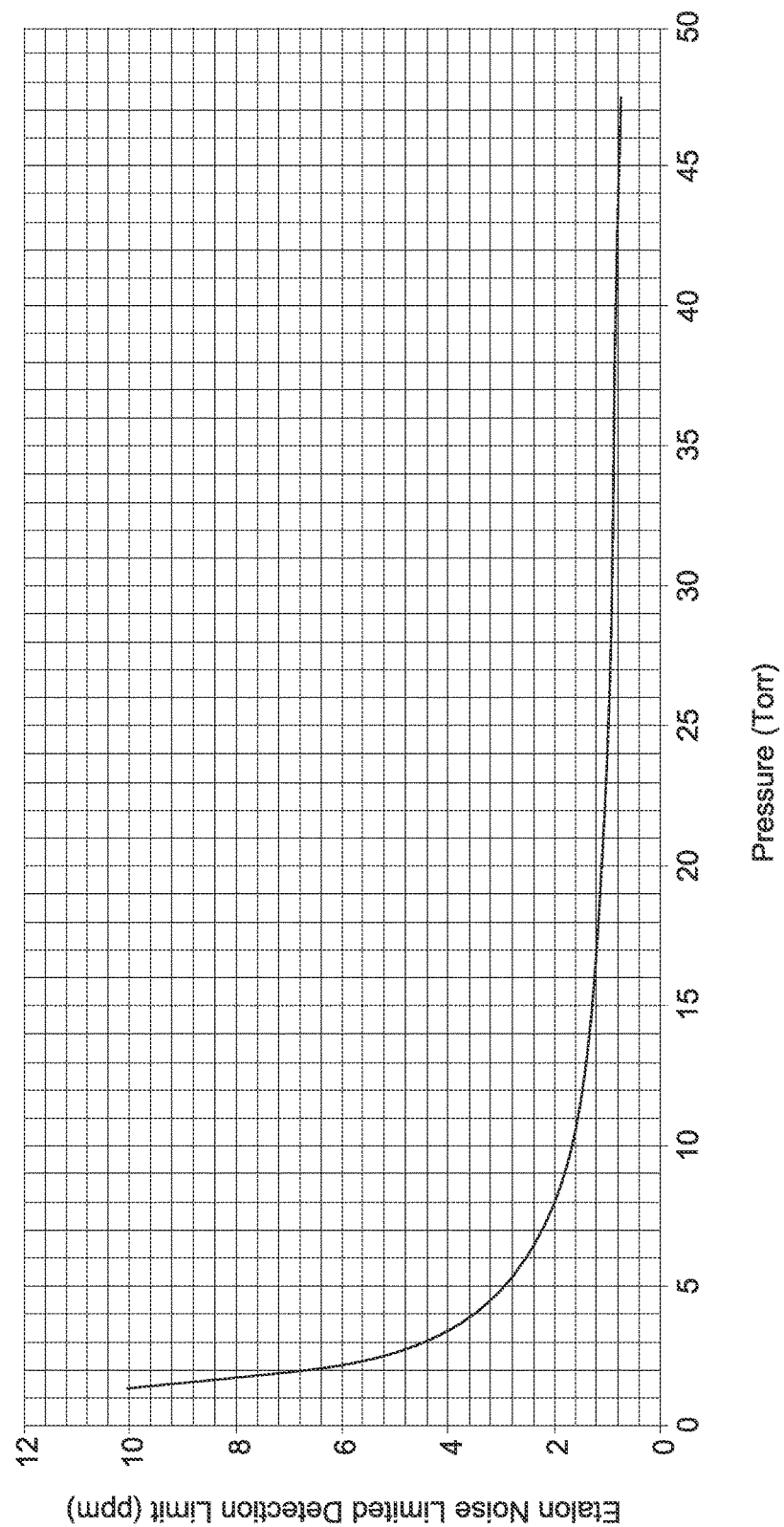
FIG. 7 is a look-up table or curve for determining an actual concentration of a primary gas in the gas mixture.

At step 606, the pressure of the gas mixture may be further pumped down to a pressure where the primary gas becomes undetectable. This pressure is referred to as a third pressure of the gas mixture. Also, at the third pressure, the second derivative of the spectra corresponding to the gas mixture may reach an elaton noise floor as depicted in FIG. 7. In addition, the detection limit variation with respect to the pressure of the primary gas may be predetermined and stored in a look up table or curve as depicted in FIG. 7. For example, the look-up curve in FIG. 7 depicts that if the determined concentration of the primary gas is 2 PPM at the sensor operating pressure or second pressure then the primary gas may start to become undetectable at the third pressure of 8 torr. In one example, the memory 412 may store a look-up table or curve that provides the concentration values of the primary gas and their corresponding pressure values at which the primary gas becomes undetectable.

Further, at step 608, the look-up table or curve may be used by the processor 412 to calculate an actual concentration of the primary gas that becomes undetectable at the recorded third pressure of the primary gas. For example, if the primary gas becomes undetectable at the third pressure of 8 torr then the actual concentration of the primary gas is expected to be 2 PPM.

Subsequently, at step 610, the calculated or actual concentration of the primary gas is compared with the measured concentration of the primary gas to determine the difference in concentration measurement of the primary gas. For example, if the measured concentration of the primary gas at the sensor operating pressure is 2.2 PPM then the primary gas is expected to become undetectable at 7 torr. However, in the current sensor measurement, the primary gas becomes undetectable at 8 torr. Thus, the processor 412 may refer to a look-up table or curve to determine that for the primary gas to become undetectable at a pressure of 8 torr, the actual concentration of the primary gas is required to be 2 PPM and not 2.2 PPM. Thus, the processor estimates an error of 0.2 PPM in the sensor measurement.

In addition, at step 612, the above steps of 602 to 610 are repeated three or more times over a period of time, to generate multiple sets of measured concentration and expected concentration values. Further, at step 614, these values are used to recalibrate the sensor unit 108 of the spectroscopy system 100.

The various embodiments of the system and the method aid in determining the concentration of the primary gas and/or secondary gas at a very low cost and high accuracy. Also, the system and method enables detection of multiple gases in a gas mixture using same light source. Additionally, the system and method enables lower detection limit of gases compared to atmospheric pressure sensor units. Moreover, the system and method includes wavelength drift correction and sensor unit calibration protocols which enables good reliability and sensor performance.

It is to be understood that a skilled artisan will recognize the interchangeability of various features from different embodiments and that the various features described, as well as other known equivalents for each feature, may be mixed and matched by one of ordinary skill in this art to construct additional systems and techniques in accordance with principles of this disclosure. It is, therefore, to be understood that the appended claims are intended to cover all such modifications and changes as fall within the true spirit of the invention.

Further, while only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method comprising:
    receiving in a cell unit a gas mixture at a first pressure comprising at least a primary gas and a secondary gas, wherein at least a first spectral line of the primary gas interferes with at least a second spectral line of the secondary gas at the first pressure of the gas mixture;
    changing a pressure of the received gas mixture in the cell unit from the first pressure to a second pressure;
    using a sensor unit for determining a spectra of the gas mixture at the second pressure, wherein at least the first spectral line of the primary gas is spectrally distinguished from at least the second spectral line of the secondary gas, wherein determining the spectra of the gas mixture at the second pressure comprises determining a derivative of the spectra effective to spectrally distinguish the first spectral line of the primary gas from the second spectral line of the secondary gas,
    identifying a peak wavelength associated with the spectrally distinguished first spectral line of the primary gas based on at least two wavelengths of the secondary gas corresponding to at least two peak amplitudes in the spectra of the gas mixture, wherein identifying the peak wavelength associated with the spectrally distinguished first spectral line of the primary gas comprises:
    selecting the at least two wavelengths of the secondary gas in the derivative of the spectra;
    adjusting the derivative of the spectra such that the at least two peak wavelengths of the secondary gas match pre-stored peak wavelengths; and
    detecting the peak wavelength associated with the spectrally distinguished first spectral line of the primary gas based on the at least two peak wavelengths of the secondary gas in the adjusted derivative of the spectra, and
    determining a concentration of the primary gas based on the identified peak wavelength associated with the spectrally distinguished first spectral line of the primary gas.

2. The method of claim 1, wherein determining the concentration of the primary gas comprises computing a peak amplitude in the derivative of the spectra at the identified peak wavelength associated with the spectrally distinguished first spectral line of the primary gas.

3. The method of claim 1, wherein determining the derivative of the spectra comprises computing a second derivative of the spectra to spectrally distinguish the first spectral line of the primary gas from the second spectral line of the primary gas.

4. The method of claim 1, wherein selecting the at least two peak wavelengths of the secondary gas in the derivative of the spectra comprises:
    searching the at least two peak amplitudes of the secondary gas in the derivative of the spectra in one or more ranges including the pre-stored wavelengths; and
    selecting the at least two peak wavelengths corresponding to the at least two peak amplitudes of the secondary gas.

5. The method of claim 1, wherein detecting the peak wavelength associated with the spectrally distinguished first spectral line of the primary gas comprises:
    searching for a peak wavelength in the adjusted derivative of the spectra within a wavelength range including a prestored peak wavelength of the primary gas; and
    representing the searched peak wavelength as the peak wavelength associated with the spectrally distinguished first spectral line of the primary gas.

6. The method of claim 1, wherein identifying the peak wavelength associated with the spectrally distinguished first spectral line of the primary gas comprises:
    selecting the at least two peak wavelengths of the secondary gas in the derivative of the spectra;
    determining spectral separation between the at least two peak wavelengths of the secondary gas; and
    identifying the peak wavelength associated with the spectrally distinguished first spectral line of the primary gas based on the determined spectral separation between the at least two peak wavelengths of the secondary gas.

7. The method of claim 6, wherein the peak wavelength associated with the spectrally distinguished first spectral line of the primary gas is identified within the determined spectral separation at a location that is corresponding to a predefined function of the determined spectral separation.

8. The method of claim 1, wherein determining the concentration of the primary gas comprises recalibrating the sensor unit to determine the concentration of the primary gas.

9. The method of claim 8, wherein recalibrating the sensor unit comprises:
    measuring an initial concentration of the primary gas at the second pressure of the gas mixture;
    reducing the pressure of the received gas mixture from the second pressure to a third pressure where the primary gas begins to become undetectable;
    calculating an actual concentration of the primary gas based on the third pressure of the gas mixture; and
    adjusting the sensor unit to measure the determined actual concentration of the primary gas at the second pressure of the gas mixture.

10. The method of claim 9, wherein calculating the actual concentration of the primary gas comprises estimating the actual concentration of the primary gas by using a pre-stored data corresponding to the third pressure of the gas mixture, wherein the pre-stored data indicates the actual concentration of the primary gas that becomes undetectable at the third pressure of the gas mixture.

11. A system comprising:
    a cell unit for receiving a gas mixture at a first pressure comprising at least a primary gas and a secondary gas, wherein at least a first spectral line of the primary gas interferes with at least a second spectral line of the secondary gas at the first pressure of the gas mixture;
    a pumping unit coupled to the cell unit for changing a pressure of the received gas mixture from the first pressure to a second pressure; and
    a control unit for:

determining a derivative of a spectra of the gas mixture at the second pressure, wherein at least the first spectral line of the primary gas is spectrally distinguished from at least the second spectral line of the secondary gas;

identifying a peak wavelength associated with the spectrally distinguished first spectral line of the primary gas based on at least two peak wavelengths of the secondary gas corresponding to at least two peak amplitudes in the derivative of the spectra; and determining a concentration of the primary gas based on the identified peak wavelength associated with the spectrally distinguished first spectral line of the primary gas, wherein the control unit further comprises a processor for:

determining the at least two peak wavelengths of the secondary gas in the derivative of the spectra;

adjusting the derivative of the spectra such that the at least two peak wavelengths of the secondary gas match pre-stored peak wavelengths; and identifying the peak wavelength associated with the spectrally distinguished first spectral line of the primary gas based on the adjusted at least two peak wavelengths of the secondary gas in the adjusted derivative of the spectra.

12. The system of claim 11 further comprising:
a light source for emitting a beam;
a beam splitter for splitting the emitted beam into a first beam and a second beam, wherein the first beam is passed through the cell unit;
a first detector coupled to the cell unit for providing a first electrical signal corresponding to the determined derivative spectra of the gas mixture to the control unit;
a second detector coupled to the beam splitter for:
receiving the second beam from the beam splitter;
providing a second electrical signal corresponding to the received second beam to the control unit.

13. The system of claim 12, wherein the control unit comprises:
an amplifying unit coupled to the first detector and the second detector for amplifying the first electrical signal and the second electrical signal;
a subtraction unit coupled to the amplifying unit for reducing noise in the amplified first electrical signal by subtracting the amplified first electrical signal with the amplified second electrical signal; and
a lock-in unit coupled to the subtraction unit for determining the derivative of the spectra of the gas mixture using the first electrical signal.

14. The system of claim 11, wherein the processor is configured to:
search at least two peak amplitudes of the secondary gas in the derivative of the spectra in one or more ranges including pre-stored wavelengths; and
select the at least two peak wavelengths corresponding to the at least two peak amplitudes of the secondary gas.

15. The system of claim 11, wherein the processor is configured to identify the peak wavelength associated with the spectrally distinguished first spectral line of the primary gas based on spectral separation between the at least two peak wavelengths of the secondary gas.

16. The system of claim 11, wherein the processor is configured to determine the concentration of the primary gas by computing peak amplitude in the derivative of the spectra at the identified peak wavelength associated with the spectrally distinguished first spectral line of the primary gas.

17. A method comprising:
receiving in a cell unit a gas mixture at a first pressure comprising at least a primary gas and a secondary gas;
using a sensor unit for determining a spectra of the gas mixture at the first pressure;
identifying, using a control unit, a peak wavelength associated with a first spectral line of the primary gas based on at least two wavelengths of the secondary gas corresponding to at least two peak amplitudes in the spectra of the gas mixture; and
determining, using the control unit, a concentration of the primary gas based on the identified peak wavelength associated with the first spectral line of the primary gas,
wherein the control unit further comprises a processor for:
determining the at least two peak wavelengths of the secondary gas in a derivative of the spectra;
adjusting the derivative of the spectra such that the at least two peak wavelengths of the secondary gas match pre-stored peak wavelengths; and
identifying the peak wavelength associated with the spectrally distinguished first spectral line of the primary gas based on the adjusted at least two peak wavelengths of the secondary gas in the adjusted derivative of the spectra.

* * * * *